US012564709B2

(12) United States Patent
Goral

(10) Patent No.: US 12,564,709 B2
(45) Date of Patent: Mar. 3, 2026

(54) PORT ADAPTED TO BE FREQUENTLY ACCESSED

(71) Applicant: SMITHS MEDICAL ASD, INC., Plymouth, MN (US)

(72) Inventor: David J. Goral, Southington, CT (US)

(73) Assignee: ICU MEDICAL, INC., San Clemente, CA (US)

( * ) Notice: Subject to any disclaimer, the term of this patent is extended or adjusted under 35 U.S.C. 154(b) by 662 days.

(21) Appl. No.: 17/926,203

(22) PCT Filed: Jun. 21, 2021

(86) PCT No.: PCT/US2021/038231
§ 371 (c)(1),
(2) Date: Nov. 18, 2022

(87) PCT Pub. No.: WO2022/005790
PCT Pub. Date: Jan. 6, 2022

(65) Prior Publication Data
US 2023/0191101 A1 Jun. 22, 2023

Related U.S. Application Data

(60) Provisional application No. 63/047,399, filed on Jul. 2, 2020.

(51) Int. Cl.
*A61M 39/02* (2006.01)

(52) U.S. Cl.
CPC . *A61M 39/0247* (2013.01); *A61M 2039/0276* (2013.01); *A61M 2039/0282* (2013.01); *A61M 2039/0288* (2013.01)

(58) Field of Classification Search
CPC ...... A61M 39/0247; A61M 2039/0276; A61M 2039/0282; A61M 2039/0288;
(Continued)

(56) References Cited

U.S. PATENT DOCUMENTS

| 4,776,843 A | 10/1988 | Martinez et al. |
| 4,804,369 A | 2/1989 | Lapeyre et al. |

(Continued)

FOREIGN PATENT DOCUMENTS

| EP | 0968026 B1 | 10/2003 |
| WO | 0139818 A2 | 6/2001 |

OTHER PUBLICATIONS

PCT International Search Report for PCT/US2021/038231 dated Oct. 12, 2021.
(Continued)

*Primary Examiner* — Courtney D Heinle
*Assistant Examiner* — Andrew Thanh Bui
(74) *Attorney, Agent, or Firm* — Louis Woo

(57) ABSTRACT

A port is adapted to be implanted to a body with its top exposed to the environment. The port has a housing defining a chamber that has an opening at the top of the housing. An aperture having a lumen attached thereto is formed at the lower portion of the chamber. For infusion, an insert that has an internal passageway that connects a fluid inlet at its top surface and a bore at its sidewall is sealingly mated to the chamber. The bore sealingly aligns with the aperture. After infusion, the insert is removed, and a blank insert is fitted to the chamber. A band of tissue ingrowth media encircles the housing to form an aseptic barrier where the outer wall of the housing and the tissue of the body encircling the housing meet.

20 Claims, 7 Drawing Sheets

(58) Field of Classification Search
CPC .... A61M 2039/027; A61M 2039/0261; A61M
2039/0258; A61M 2039/0264
See application file for complete search history.

(56) References Cited

U.S. PATENT DOCUMENTS

| 5,474,526 | A | 12/1995 | Danielson et al. | |
|---|---|---|---|---|
| 7,811,257 | B2 * | 10/2010 | Saab ................. | A61M 25/0097 |
| | | | | 604/539 |
| 8,021,340 | B2 | 9/2011 | Porter et al. | |
| 8,974,422 | B2 * | 3/2015 | Gill ................... | A61M 39/0247 |
| | | | | 604/513 |
| 9,226,849 | B2 | 1/2016 | Staggs | |
| 2008/0108954 | A1 | 5/2008 | Mathias et al. | |
| 2011/0034852 | A1 | 2/2011 | Hausler et al. | |
| 2012/0053673 | A1 * | 3/2012 | Golding ........... | A61M 39/0247 |
| | | | | 623/1.15 |
| 2013/0072847 | A1 | 3/2013 | Schutz et al. | |
| 2019/0167964 | A1 | 6/2019 | Lewis et al. | |
| 2020/0155003 | A1 * | 5/2020 | Mitchell ............... | A61B 5/1118 |
| 2022/0105332 | A1 * | 4/2022 | Bizup ............... | A61M 39/0208 |

OTHER PUBLICATIONS

PCT Written Opinion for PCT/US2021/038231 dated Oct. 12, 2021.
NIH Publication "Effects of pore size, implantation time and nan0-surface properties on rat skin ingrowth into percutaneous porous titaium implants" J. Biomedi Mater Res A. May 2014.
PCT Notification of International Preliminary Report on Patentability for PCT/US2021/038231 dated Jan. 12, 2023.
PCT International Preliminary Report on Patentability for PCT/US2021/038231 dated Jan. 12, 2023.
EPO Communication dated Oct. 12, 2023 for EP application No. 21833825.9.

* cited by examiner

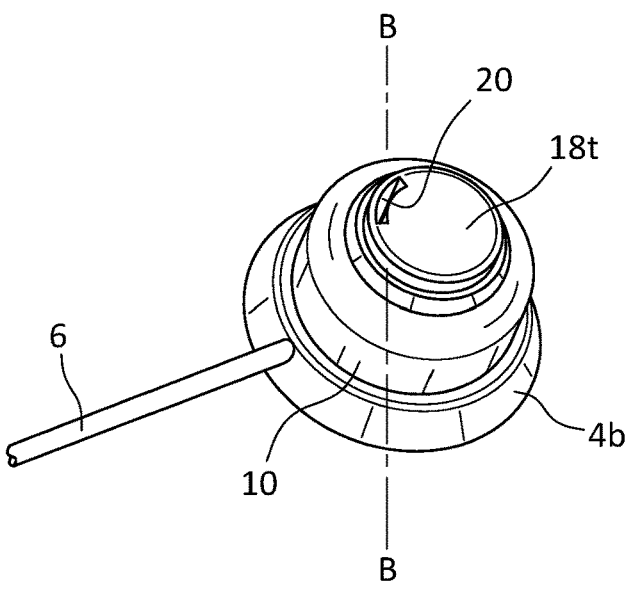
FIG. 6A
FIG. 6B
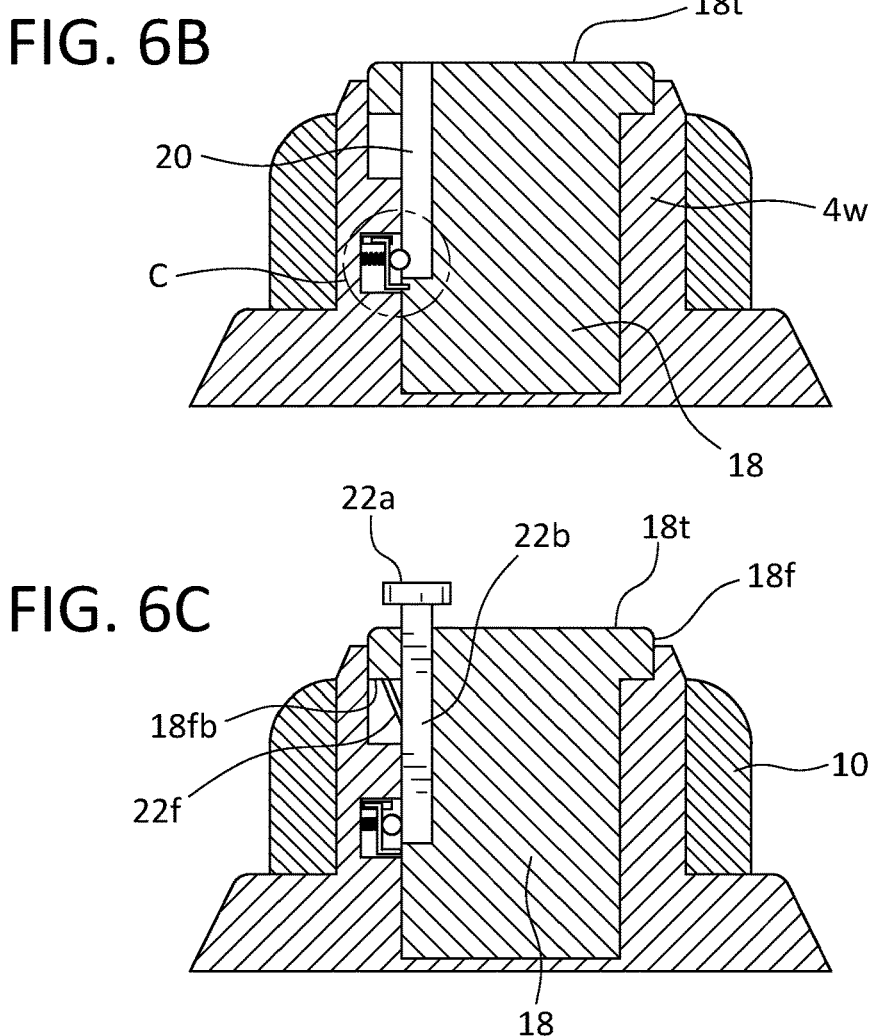
FIG. 6C

PORT ADAPTED TO BE FREQUENTLY ACCESSED

FIELD OF THE INVENTION

The present invention relates to ports that are adapted to be implanted into patients and more particularly a port that is adapted to be partially implanted into the patient and can be accessed frequently without using needles.

BACKGROUND OF THE INVENTION

Portals or ports are usually implanted subcutaneously into patients and are used to convey fluid stored in their reservoirs to locations inside the patients such as the vasculature system of the patients. With the current crop of implantable ports, once the port has been implanted into a patient, the biggest downside is that the clinician has to use a needle or cannula to pierce through the skin of the patient in order to access the port reservoir. Such piercing of the patient does not favor certain things that may need to be done such as frequent access of the port, for example in a procedure such as dialysis where the implanted port needs to be accessed frequently oftentimes multiple times a week. Such frequent access prevents the site where the needle inserts into the patient from healing, which in turn may lead to infection of the site.

Another downside to conventional implanted ports is that a port, once implanted into a patient, has to be located. One conventional method is to palpate the area of the patient where the port is implanted to locate the port. Other methods include providing an indicia on or into the port to enable the port to be viewed under x-ray or radiographic imaging. To pinpoint the septum of the port where the needle needs to pierce into after the needle is inserted into the patient, an impression(s) together with a radiopaque indicia may be provide to the septum of the port. Such pinpointing of the septum of an implanted port is described in U.S. Pat. Nos. 8,092,435, 8,535,281 and 9,950,150, all assigned to the assignee of the instant application. The respective disclosures of the '435, '281 and '150 patents are incorporated by reference to the specification of the instant application.

There is therefore a need for a port that can be readily located and frequently accessed without the skin of the patient having to be pricked and pierced repeatedly at the port site, and yet remains aseptic even though adapted to be frequently accessed.

SUMMARY OF THE PRESENT INVENTION

The port of the instant invention has a housing that is adapted to be substantially implanted into a patient. The interior of the housing defines a chamber. An opening at the top of the housing exposes the chamber to the environment. An aperture is formed at the lower portion of the chamber and extends through the wall of the housing. The aperture is of a dimension that enables a lumen or catheter to extend from the inside the chamber to outside the housing. A guiding formation may be provided at the wall portion where the aperture is formed to enable a base, for example a flange, of the lumen to be anchored to the housing. An alternative embodiment may have an outer lumen fixedly attached to the aperture so that an inner lumen for example a catheter may extend along the fixed lumen. Either case, it is envisioned that the lumen, if not attached, is replaceable with another lumen after use; and if the outer lumen is fixedly attached to the housing, then the inner lumen is replaceable with another inner lumen after use.

Removably and sealingly fitted to the chamber of the housing is an insert or plug. The height of the insert may be such that when it is fully mated into the chamber, its top surface would be substantially flush with the top of the housing that peripherally surrounds it. When the port is used for infusion, the insert would have an internal passageway that extends between an infusion fluid inlet at its top surface and a bore at a sidewall of the insert. The insert may have a substantially lengthwise guide formation at its outer peripheral surface that complements a guide formation at the inner wall of the housing, so that the insert may be sealingly fitted into the housing at a predetermined orientation relative to the housing. This ensures that the bore at the insert comes into alignment with the proximal or base opening of the lumen that is attached to the aperture of the housing. For ease of discussion, the insert with the internal passageway may be referred to as an infusion plug or infusion insert.

The housing of the port is adapted to be implanted into the body of a patient to a depth that exposes at least the top surface of the insert. The lumen of the housing may be selectively positioned inside the patient, for example a vein, artery or somewhere in the vasculature system or an organ of the patient, with the implantation of the housing. When a fluid store is connected to the fluid inlet at the top surface of the infusion insert, the fluid path established by the passageway in the infusion insert and the lumen extending out of housing into the patient would convey the fluid medicament from the fluid store to the selected location in the patient.

After infusion, the infusion insert with the internal passageway may be removed from the housing and be replaced by a blank insert with no internal passageway that sealingly but removably plugs the chamber, i.e., a blank insert or insert plug that seals the chamber of the housing. The infusion insert may then be disposed of. The blank insert is replaced with a clean infusion insert when infusion is next needed. Likewise, the lumen connected to the housing may be replaced by a clean lumen. If the lumen is fixedly attached to the housing aperture and acts as an outer lumen, then the used and therefore contaminated inner lumen or catheter that fits along the outer lumen is removed and a new inner lumen is slidably fitted along the outer lumen.

To prevent infection at the area where the housing of the port meets the body of the patient, at least one band of tissue ingrowth media is attached to and encircles the outer wall of the housing to form an aseptic barrier where the outer wall of the housing and the tissue of the body of the patient that encircles the port housing meet.

The present invention accordingly relates to a port comprising: a housing having an interior defined by a bottom, a non-ending wall and a top that has an opening that opens to the interior of the housing; at least one aperture at a selected location through the non-ending wall; an insert having a top surface and a cross dimension that enables it to matingly fit to the interior of the housing via the opening of the housing, the top surface of the insert in substantial planar relationship with the top of the housing after insertion to the housing; wherein the housing of the port is adapted to be implanted into a body with the top surface of the insert exposed to environment.

The present invention further relates to a port adapted to be implanted into a body while leaving a portion thereof viewable visually, comprising: a housing having an interior defined by a bottom, a non-ending wall having an outer surface and a top that has an opening that opens to the interior of the housing; at least one lumen extending from at least one aperture at the non-ending wall away from the housing; an insert having a top surface and a cross dimension that enables it to matingly fit to the interior of the housing via the opening of the housing; wherein the housing of the port is implantable into a body to a depth where the top surface of the insert remains outside the body or at skin level so as to be viewable visually.

The present invention furthermore relates a port viewable visually and accessible from environment after implantation, comprising: a housing having an interior defined by a bottom, a non-ending wall having an outer surface and a top that has an opening that opens to the interior of the housing; at least one lumen extending from at least one aperture at the non-ending wall; tissue ingrowth media encircling the outer surface of the non-ending wall; an insert having a top surface and a cross dimension that matingly fits into the interior of the housing via the opening of the housing; wherein housing of the port is implantable into a body to a depth where the top surface of the insert remains accessible from the environment; and wherein once implanted to the body, the tissue ingrowth media forms an aseptic barrier between the non-ending wall and tissue of the body encircling the wall.

BRIEF DESCRIPTION OF THE FIGURES

The present invention will become apparent and the invention itself will be best understood with reference to the following description of the invention taken in conjunction with the accompanying drawings, wherein:

FIG. 6A is a perspective view of a variation of the inventive port showing a blank insert having a bore for use in removing the insert from the housing;

FIG. 6B is a cross-sectional view of the port shown in FIG. 6A along line B-B;

FIG. 6C shows an exemplar tool mated to the FIG. 6 port to remove the insert from the housing;

DETAILED DESCRIPTION OF THE INVENTION

Figure 1A:
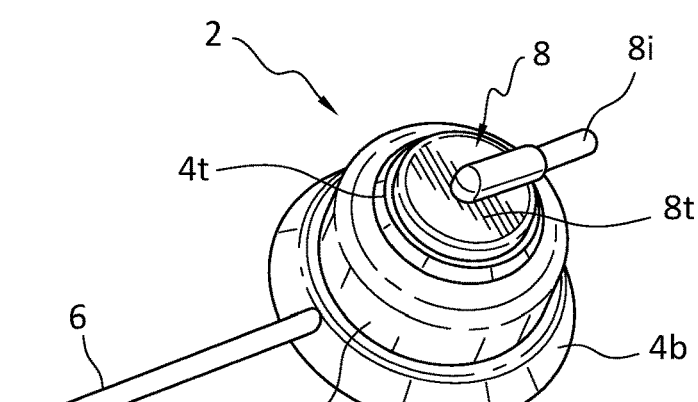
FIG. 1A is a perspective of an embodiment of the port of the present invention.
Figure 1B:
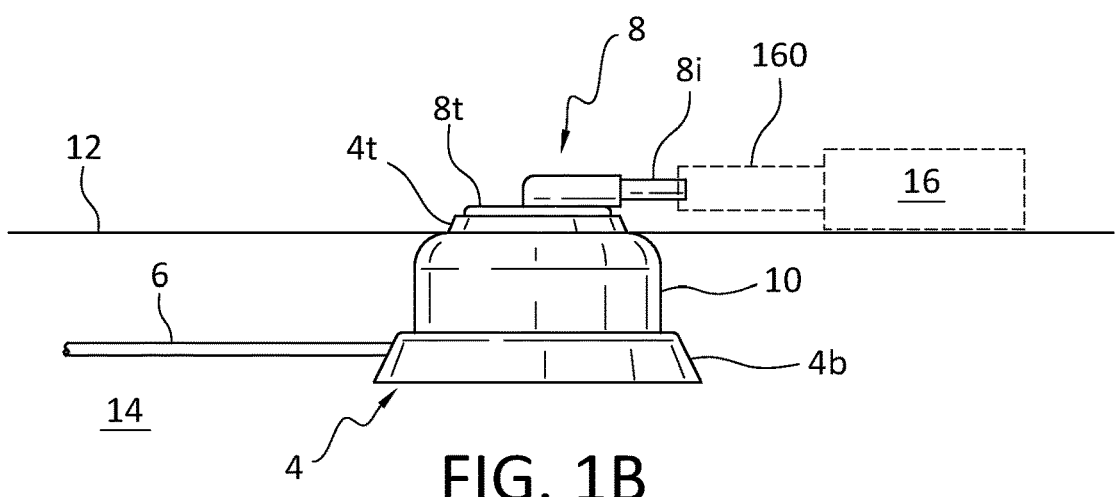
FIG. 1B is a side view of the embodiment of the port of FIG. 1A.
Figure 1C:
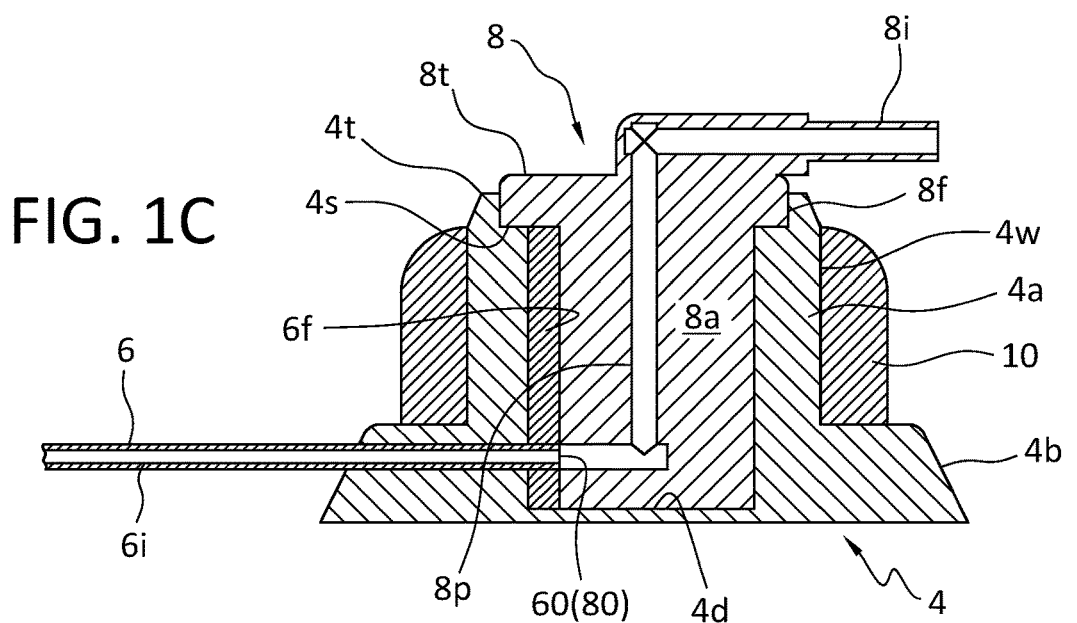
FIG. 1C is a cross-sectional view of the embodiment of the port of FIG. 1A.

With reference to FIGS. 1A-1C, 2 and 3A-3B, the inventive percutaneous portal or port 2 is shown to include a housing 4, which has a main or upright portion 4a and a base 4b. The upright portion 4b is formed by a non-ending wall 4w that, for the exemplar embodiment shown, is a circumferential wall. Wall 4w extends upwardly from base 4b to a top portion 4t of housing 4 that has a downward taper. For ease of discussion, top portion 4t may be considered to be the top surface of housing 4 and may simply be referred to as top 4t.

Figure 2:
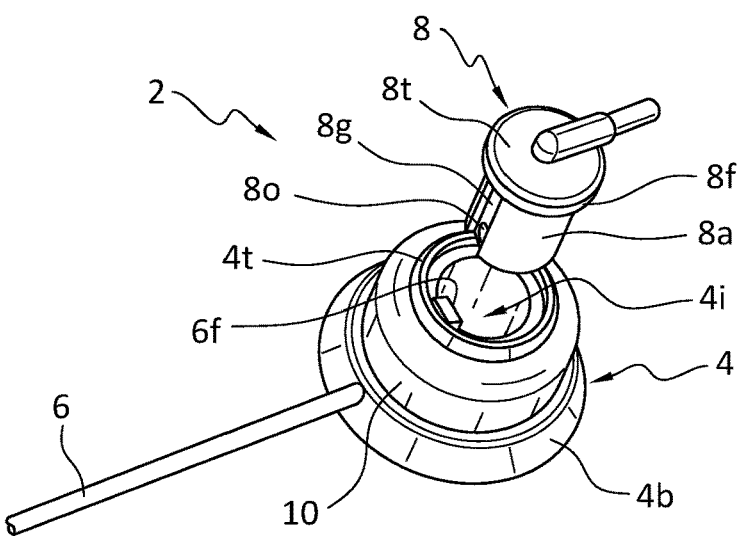
FIG. 2 is a dissembled perspective view showing the components of the present invention port.
Figure 3A:
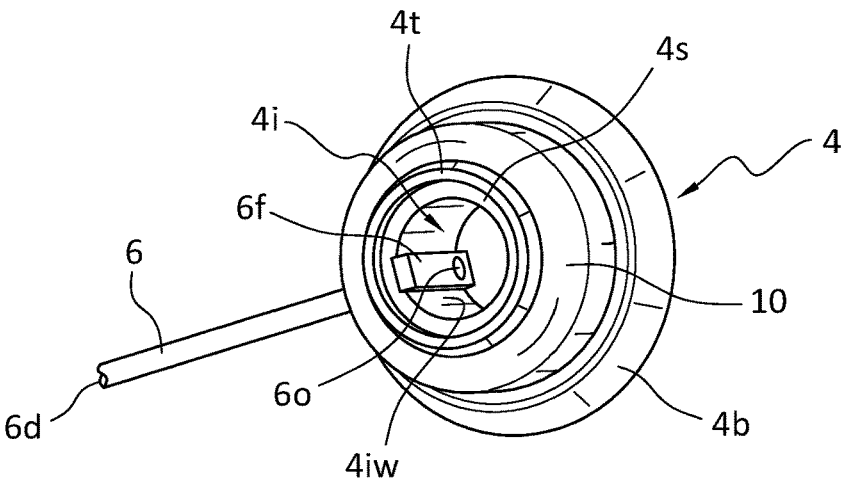
FIGS. 3A-3B are perspective views showing the interior chamber of the housing of the port of the present invention.
Figure 3B:
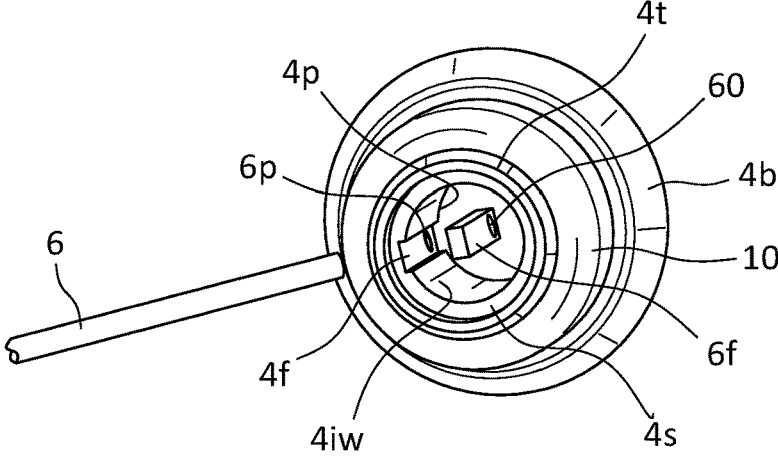

As best shown in FIGS. 2 and 3A-3B, top 4t of housing 4 is opened to the interior 4i of housing 4. Another way of looking at it is that the interior of housing 4 is a chamber 4i that is defined by the inside circumferential or interior wall 4iw and a bottom 4d of housing 4, with its top opened to the environment. A non-ending shoulder or step 4s forms a short distance from top 4t along the interior wall 4iw that defines chamber 4i. Housing 4 may be formed from a number of inert plastic or metallic materials as is well known in the manufacture of ports.

As best shown in FIG. 3B, housing 4 further has an aperture 4p through a lower portion of wall 4w that extends through base 4b. A tube, tubing or lumen 6 slidably and fittingly extends through aperture 4p with its distal end 6d selectively positionable to a location in the body of a patient. Thus, the output of the lumen may be directed to any selected organ or the veins and arteries of the vasculature system of the patient as is well known, after the housing 4 is percutaneously implanted into the patient. Lumen 6 may be any tube, tubing or catheter that are known to be used for infusion or withdrawing of fluid. For the exemplar embodiment, the proximal end 6p of lumen 6 merges into a key flange 6f that has an opening 6o which forms the base or proximal opening of lumen 6. An internal formation 4f is formed at the interior wall 4iw that includes aperture 4p, and has a dimension that enables flange 6f of lumen 6 to form fit thereto, as per shown in FIGS. 3A-3B. For the embodiment shown in FIGS. 3A-3B, given that lumen 6 is not fixedly attached to housing 4, a used lumen may be readily replaced with a new one, as will be described further infra.

Port 2 also includes an insert 8 that may be in the form of a plug that is adapted to fittingly and sealingly mate to the interior or chamber 4i of housing 4. Insert 8 may be manufactured from a number of plastic and metallic materials that are known to be use in the manufacture of ports. Insert 8 may henceforth be referred to as an insert, a plug or a plug insert.

As best shown in FIGS. 1A-1C and 2, insert 8 has a main body 8a which, for the exemplar embodiment shown, is in the form of a cylindrical body structure or simply a cylinder that has cross dimension and length that allow the insert to be sealingly and slidably mated or fitted into the interior or chamber 4i of housing 4. A guide slot 8g is formed along the outer surface of insert 8 so that insert 8 may be guided along by flange 6f as it is inserted into chamber 4i, assuming that lumen 6 has been fully slid fitted to aperture 4p of housing 4.

In addition to acting as a guide for insert 8 into housing 4, flange 6f coacts with slot 8g to prevent relative rotation between insert 8 and housing 4. Insert 8 has an upper lip or flange 8f under which the cylindrical body 8a integrally hangs. Insert 8 is fully inserted into housing 4 when its lip 8f meets step 4s of housing 4. When thus fully mated to chamber 4i, only the top surface 8t of insert 8 is exposed to the environment.

For infusion and other procedures where fluid medicament is to be infused to a patient or bodily fluid from the patient be withdrawn, a through passageway 8p is formed in insert 8. Passageway 8p extends from the top surface 8t of insert 8 to an opening 8o in guide slot 8g. Opening 8g is formed at a location in slot 8g such that it comes into sealing alignment with proximal opening 6o of lumen 6 when plug 8 is fully mated to housing 4, as per shown in FIG. 1C. It should be appreciated that opening 80 does not have to be formed in slot 8 so long as it is located such that it comes into alignment with the inlet of a lumen or catheter that outputs the fluid. For example, a complementary guiding arrangement for the housing and insert may be provided away from where the inlet of the lumen meets the outlet of the passageway were the lumen fixedly attached to the housing or that the base flange of the lumen fits to the aperture and is flush with the interior wall of the housing.

To facilitate infusion of fluid, an infusion inlet or fluid inlet 8i is provided or formed at the top surface 8t of insert 8. As is well known, inlet 8i is adapted to be coupled to an outlet of a fluid store so that the medicament stored in the fluid store may be conveyed through passageway 8p and the internal passage 6i of lumen 6 for output to the location inside the patient where the distal end of the lumen is selectively located.

At least one band of tissue ingrowth media 10 attachedly encircles the outer circumferential surface of upright wall 4w of housing 4. The tissue ingrowth media may be any of the bio-materials available and may include polymers, tantalum, titanium, ceramics and other materials that demonstrate integration sufficient with the skin to prevent bacterial penetration. An exemplar tissue ingrowth media that may be used to encircle housing 4 of port 2 may be a porous titanium mesh structure that may have pore size 40-160 μm, and preferably between 40-100 μm. By having the porous bio-material sealingly surrounding at least the upright wall 4w of housing 4, tissue ingrowth is effected when the housing of the port is percutaneously implanted into a patient and the pores of the material are filled by fine fibrovascular tissue growing and extending into the pores. As a result, after sufficiently healing, the ingrowth media interface between the port and the tissue of the patient that surrounds the housing of the port forms an aseptic barrier between the port and the tissue to prevent the risk of infection to the patient. A more detailed description of the effect of pore size in porous implants is provided in the article entitled "Effects Of Pore Size, Implantation Time And Nano-surface Properties On Rat Skin Ingrowth Into Percutaneous Porous Titanium Implants", by Brad J. Farrell et. al., *J Biomed Matter Res. A.* 2014 May; 102(5): 1305-1315.

The inventive port 2 may be used for infusing fluid medicament to a patient. In operation, port 2 is percutaneously implanted into the body 14 of the patient at a depth where the top 4t of housing 4 and the top 8t of insert 8 are at or above the skin 12 of the patient, as per shown in FIG. 1B. The top surface 8t of the insert, along with its fluid inlet 8i, thus are exposed to the environment. Fluid inlet 8i may be coupled to a fluid outlet 16o of a fluid store 16 (shown in dotted line in FIG. 1B) that may be a syringe, a fluid pump, a fluid bag, a fluid collection reservoir, or other types of fluid storage devices as is well known. Port 2 may be sutured to the patient as is conventionally known. Alternatively, the port may be adhesively secured to the patient by using a tissue adhesive such as the 3M VETBOND tissue adhesive, or by using an adhesive tape.

With the top of the port exposed, an advantage of the present invention is that there is no longer any need for needles to pierce the skin and puncture the patient, since the inventive port has no septum to be pierced. Thus, without causing additional discomfort or risking infection to the patient, the port can be frequently accessed. Another advantage is that a clinician can accurately determine visually where the port is located since the top of the port is exposed. Yet another advantage is that the components of the port, other than the implanted housing, can be readily replaced after use. This is significant insofar as conventionally if a component of an implanted port becomes defective or worn out, the clinician would need to surgically removed the defective port and replace it with a new one. But since the top of the port is exposed to the environment, the insert as well as the lumen are readily replaceable so that the integrity of the components of the port are maintained. Furthermore, procedures that require the infusion of fluid into and/or withdrawal of fluid from a patient can be expedited since there is no need to located the port, pierce the septum and then connect the inserted needle to the fluid store as were done conventionally.

Figure 4A:
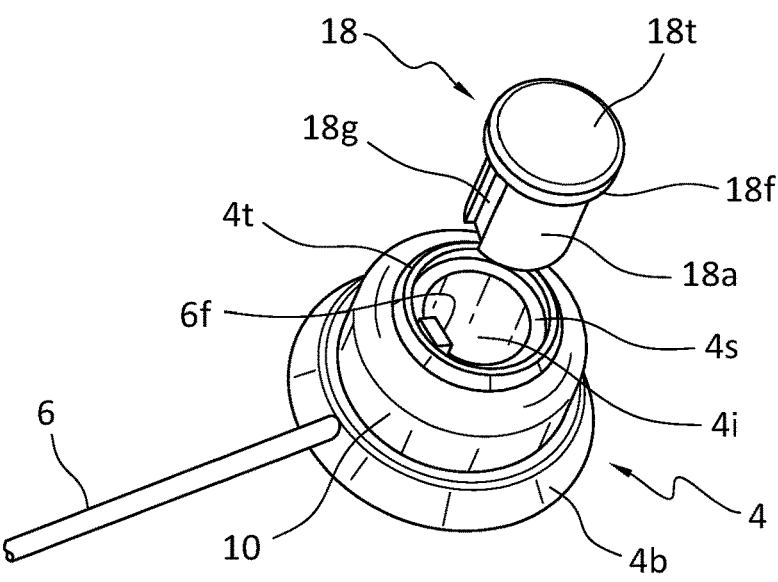
FIG. 4A is a dissembled perspective view showing the components of another embodiment of the present invention port.
Figure 4B:
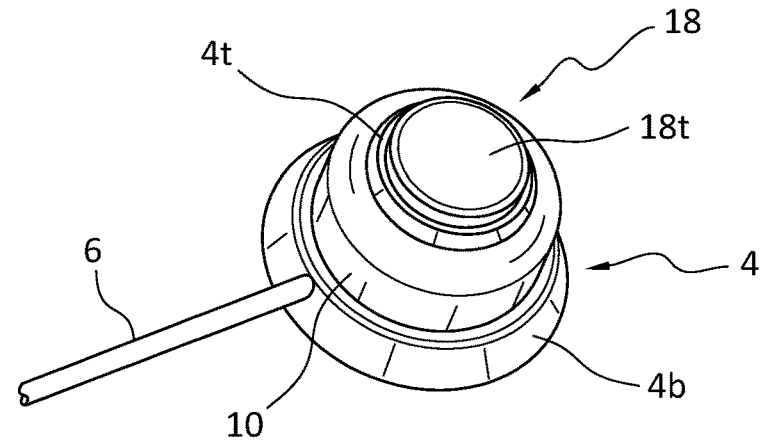
FIG. 4B is a perspective view of the assembled embodiment port shown in FIG. 3A.
Figure 4C:
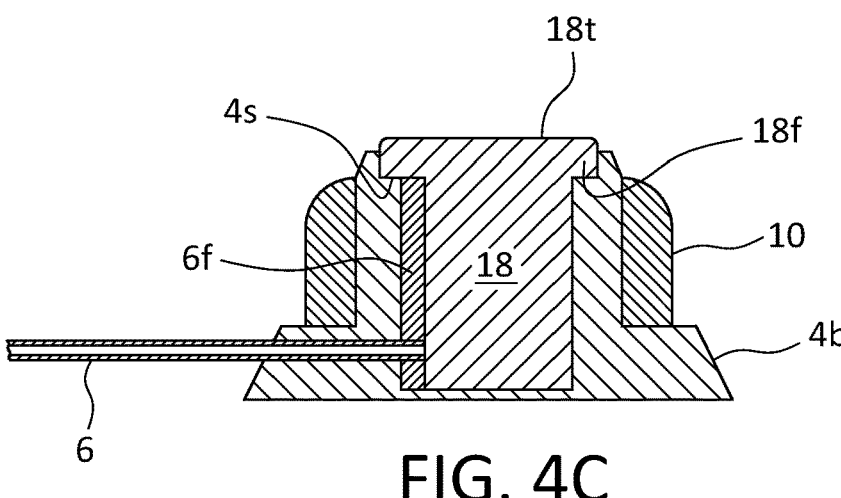
FIG. 4C is a cross-sectional view of the port shown in FIG. 4B.

Once a procedure, for example infusion, is finished, instead of leaving insert 8 in housing 4 and expose the port to the risk of infection due to the fluid store having now been disconnected from the fluid inlet 8i, insert 8 may be removed and be replaced with a blank insert or plug. The inventive port may also be fitted with a blank insert during shipping and possibly during the implanting procedure, as the blank insert may be replaced with an infusion insert, after the housing of the port is properly implanted into the patient, as per discussion above. The blank insert and its fitting into the housing of the port are shown in FIGS. 4A-4C. For FIGS. 4A-4C and the remaining figures of the specification, components that are the same as those shown in and described with reference to FIGS. 1A to 3B are labeled the same.

With reference to FIGS. 4A-4C, a blank insert of plug 18 is shown. Other than the infusion inlet, plug 18 has the same external configuration as insert 8 including a cylindrical body 18a. Internally, plug 18 is solid and has no internal passageway. Externally, plug 18 has a top surface 18t, a flange 18f extending downwardly from top surface 18t for seating onto step 4s of housing 4 when plug 18 is sealingly and fully inserted into the interior chamber 4i, and a slot 18g along a sidewall that guides plug 18 into the housing. FIG. 4A shows plug 18 superposed over housing 4 and ready to be inserted thereinto. FIG. 4B shows plug 18 to be sealingly and fully inserted into the housing 4, and FIG. 4C is a cross-sectional view of the inventive port fitted with plug 18. The color of at least the top surface of plug 18 may be matched to skin tones. An additional cover over the exposed portion of the port that may include the periphery of the housing that surrounds the plug provides an additional level of protection against contamination. With port 2 as shown in FIGS. 1A and 4B implanted into the patient, there is a reduced risk of infection to the patient since the tissue ingrowth media 10 acts as an aseptic barrier to germs and bacteria to where the wall of the housing and the tissue of the patient meets, and the blank plug acts to block germs and bacteria from entering the chamber of the housing.

As discussed above, components of the inventive port, once used, can be exchanged or replaced with new ones. The exchange or replacement of a contaminated lumen with a new lumen may be gleaned from FIGS. 3A-3B, where a (presumably contaminated) lumen 6 may be removed from aperture 6p and be replaced with a new lumen. An alternative to the removable lumen is to fixedly attach an outer lumen or tubing to housing 4, and have an inner lumen, tubing or catheter slidably fitted along the outer lumen. If the outer lumen extends from the internal formation 4f at housing 4, then the removable inner lumen may have a member similar to flange 6f at its proximal end. That way, the outer lumen would guide the distal end of the inner catheter fitted therealong to the selected area of the patient where infusion or withdrawal of fluid takes place. Once the procedure is finished, the used inner catheter may be replaced with a new one.

Figure 5A:
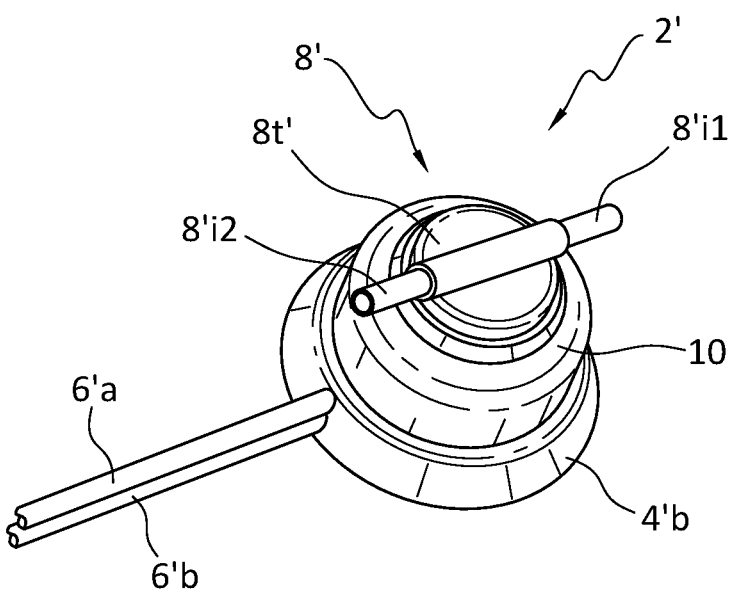
FIGS. 5A-5B show a further embodiment of the port of the present invention where the insert has multiple passageways.
Figure 5B:
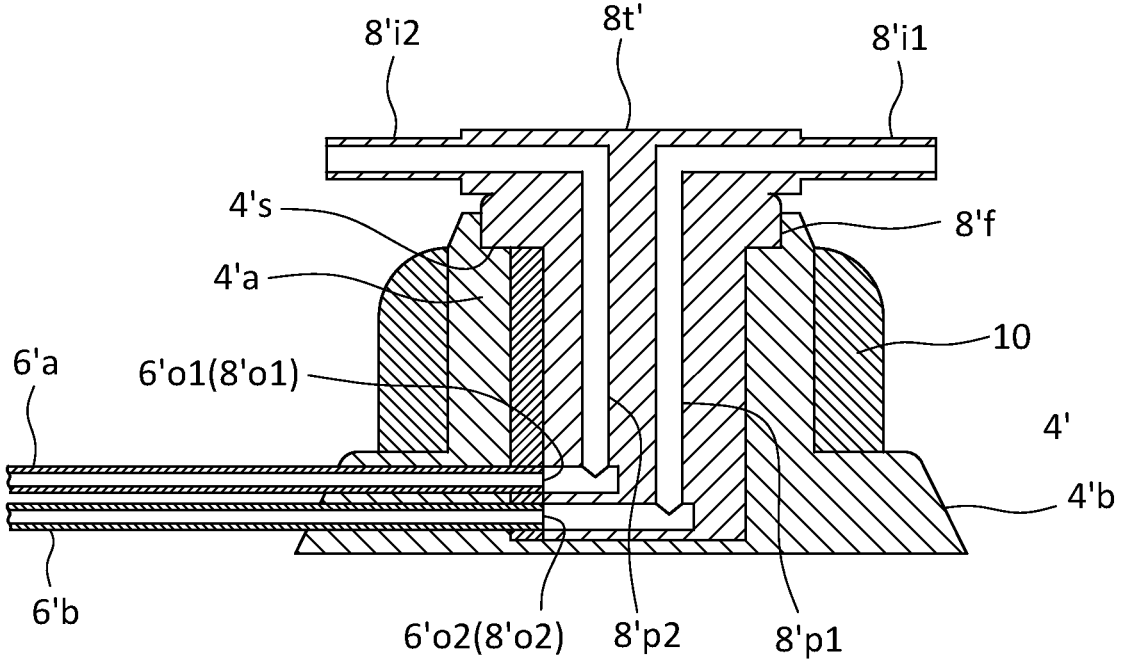

FIGS. 5A-5B illustrate an alternative embodiment of the inventive port where multiple passageways are provided in the insert plug for establishing multiple fluid paths. For the exemplar embodiment shown, insert 8' of port 2' has two fluid passageways 8'p1 and 8'p2 connected to fluid inlets 8'i1 and 8'i2, respectively, at the top surface of insert 8'. Passageways 8'p1 and 8'p2 have respective outlets 8'o1 and 8'o2 that are in alignment with corresponding proximal openings 6'o1 and 6'o2 of lumens 6'a and 6'b at base 4'b of housing 4'. The exemplar multiple lumens port may be used for procedures such as dialysis where separate fluid paths are needed to infuse fluid into the patient as well as withdraw fluid from the patient. Although shown to have two fluid paths, the insert of the instant invention may be configured to have more than two passageways by possibly increasing the dimension of the plug and the housing, if necessary. A band of tissue ingrown media 10 encircles wall 4'a of housing 4' to establish an aseptic barrier to prevent infection to the patient, as discussed above.

To ensure that the insert, be it the infusion plug or plug, not be inadvertently removed from the housing of the port, an exemplar locking mechanism is provided to fixedly maintain the insert and the housing together, once the insert has been mated to the housing, until such time as the insert is to be purposely removed from the housing. The locking mechanism is described with reference to FIGS. 6A-6F which illustrate the inventive port having a plug fitted to the housing in the manner as shown in FIGS. 4B-4C. In FIGS. 6A-6F, components that are the same as in FIGS. 4B-4C are labeled with the same reference numbers.

As shown in FIG. 6A, on top surface 18t of plug 18 is an orifice that opens to a bore 20 that has a semi-circular cross configuration that matches the curvature of the outer circumferential surface of the cylindrical body 18a of plug 18. Bore 20 extends longitudinally along a sidewall of insert 18 offset from flange 6f of lumen 6, and therefore does not affect the coacting guiding relationship between flange 6f and slot 18g as discussed above.

Figures 6D, 6E, 6F:
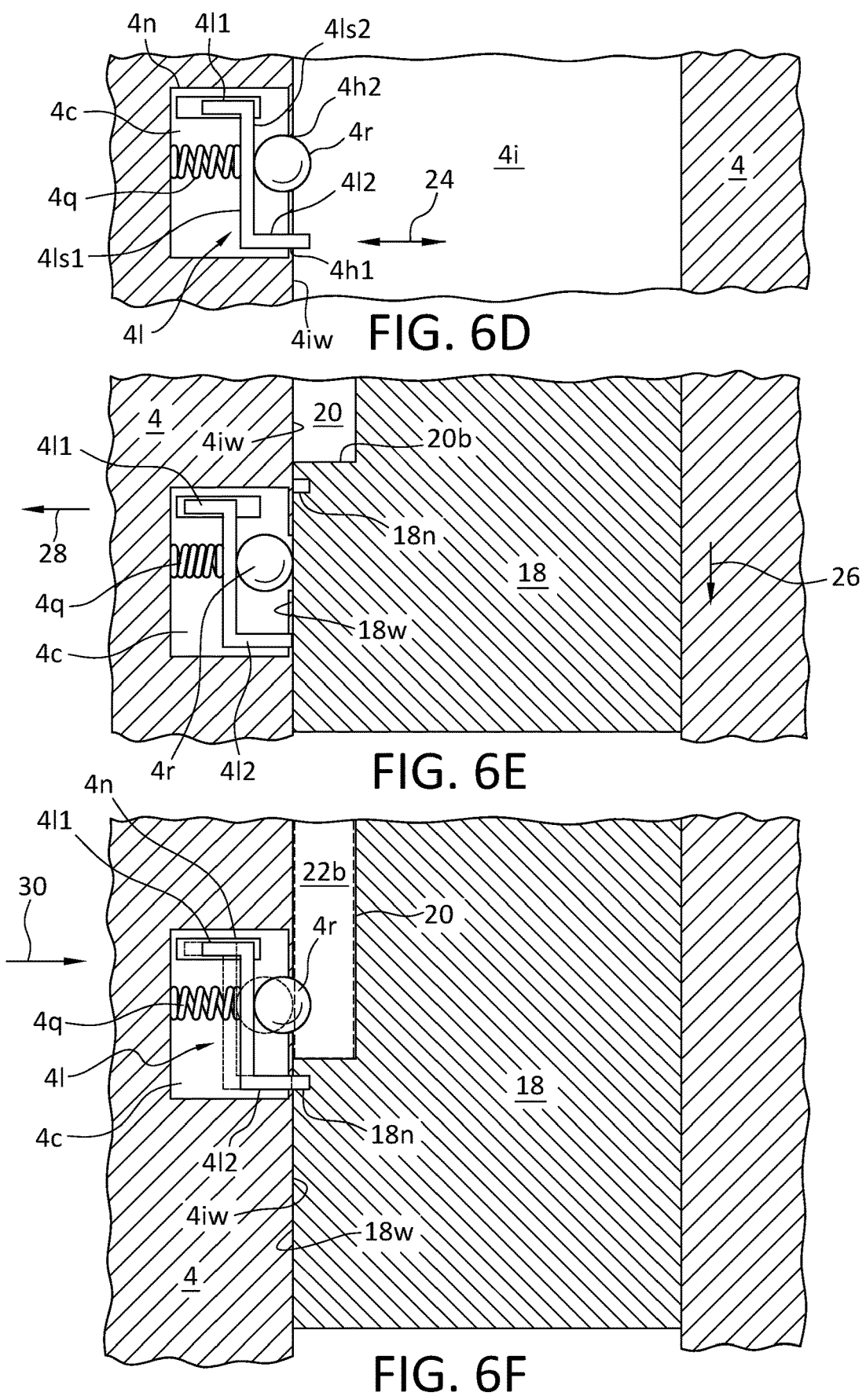
FIG. 6D is an enlarge view of one portion of the locking mechanism shown in FIGS. 6B-6C.
FIG. 6E shows the reaction of the locking portion at the housing as an insert is fitted into the housing.
FIG. 6F illustrates the working relationship between the insert of FIG. 6E and the respective locking portions of the locking mechanism in the housing and the insert of the port of FIG. 6A.

As shown in FIG. 6B, bore 20 extends from top surface 18t to a depth past a location at wall 4w of housing 4 in an area defined by dotted circle C. An enlarged view of circle C is illustrated in FIG. 6D showing a cavity 4c that houses a biasing element 4q for example a spring that biases against a back surface 4ls1 of the main body of a cantilever member 4l. Member 4l has a first leg 4l1 slidably supported in a channel 4n and a reversed direction second leg 4l2 adapted to move bidirectionally as per indicated by directional arrow 24 in and out of an opening 4h1 at the interior wall 4iw. A ball bearing or roller ball 4r is in pressing contact with the front surface 4ls2 of cantilever member 4l in opposed position to biasing member 4q. Ball 4r is adapted to move bidirectionally into and out of the interior 4i of housing 4 via an opening 4h2. Member 4l, biasing element 4q and ball 4r together may be considered a first locking portion of the locking mechanism of the inventive port. FIG. 6D shows that ball 4r and leg 4l2 each extend out of wall 4iw into the interior chamber 4i of housing 4 when there is no insert in chamber 4i. It should be appreciated that the dimensions of the components shown in FIG. 6D, and also FIGS. 6E-6F to be discussed below, may be exaggerated to better illustrate the invention and may therefore not to scale.

FIG. 6E shows the mating of plug 18 into chamber 4i of housing 4 in the direction of the directional arrow 26. Insert 18 includes bore 20 as discussed above with reference to FIG. 6A-6B. In addition, there is a notch 18n proximate to the bottom 20b of bore 20. The location of notch 18n along insert 18 is predetermined to be such that notch 18n would accept leg 412 when ball 4r is biased by biasing element 4q fully into bore 20 as per shown by the solid line illustration of FIG. 6F. Notch 18n may be considered the second locking portion of the locking mechanism of the inventive port. As shown in FIG. 6E, as insert 18 is moved along the direction indicated by directional arrow 26, the outer surface of its sidewall 18w comes into contact with ball 4r to bias ball 4r in the direction as indicated by directional arrow 28 so that both ball 4r and leg 412 remain retracted in cavity 4c. So long as interior wall 4iw and sidewall 18w are in sliding contact with each other, ball 4r and leg 412 remain in cavity 4c. It should be appreciated that the gap shown between the surface of the interior wall 4iw of housing 4 and the outer surface of wall 18w shown in FIG. 6E (and FIG. 6F) is for illustration purpose only, for in actuality, depending on acceptable tolerances for sealing, the respective wall surfaces of the housing and the insert may be in sliding contact with each other.

FIG. 6F shows insert 18 fully mated into interior chamber 4i of housing 4. As shown, ball 4r moves from its retracted position as indicated by its dotted line representation along the direction indicated by directional arrow 30 partially into bore 20. Correspondingly, the front end of leg 4l2 is positioned inside notch 18n, so that the respective positions of ball 4r and leg 4l2 are as shown in FIG. 6D. As a result, insert 18 and housing 4 are fixedly held or maintained to each other so that the insert cannot be inadvertently removed from the housing. The same exemplar locking mechanism may be provided to the infusion insert to prevent its accidental removal from the port housing.

To remove the exemplar plug 18 (or a locked infusion insert 8) from the housing 4, an exemplar removal tool as per shown in 7A-7B may be used. In particular, tool 22 is shown to have a handle 22a and a body 22b each curved slightly to match the curvature of bore 20. The length of tool 22 is such that its distal end 22d comes into contact with the bottom 20b of bore 20 to prevent further downward movement of tool 22. A finger 22f naturally pointing away from body 22b extends at a location opposing a space 22s at body 22b just below the bottom surface 18fb (FIG. 6C) of flange 18f when tool 22 is fully inserted into bore 20. Thus, as tool 22 is inserted into bore 20, finger 22f is forced by interior wall 4iw into space 22s until the tip of finger 22f passes the bottom surface 18fb of flange 18f, at which time finger 22f returns to its natural position underneath bottom surface 18fb, as per shown in FIG. 6C. At or just prior to finger 22f coming into contact with bottom surface 18fb, the distal portion of body 22b comes into contact with ball 4r to bias it and leg 412 into cavity 4c of housing 4. Plug 18 can then be removed by pulling tool 22 upwards by its handle 22a. The removed insert may be discarded along with tool 22. An infusion insert having the exemplar or similar locking mechanism may be removed the same way. Tool 22 should only be available to the clinician or nurse to prevent tampering of the port.

9

Figures 7A, 7B, 8A, 8B:
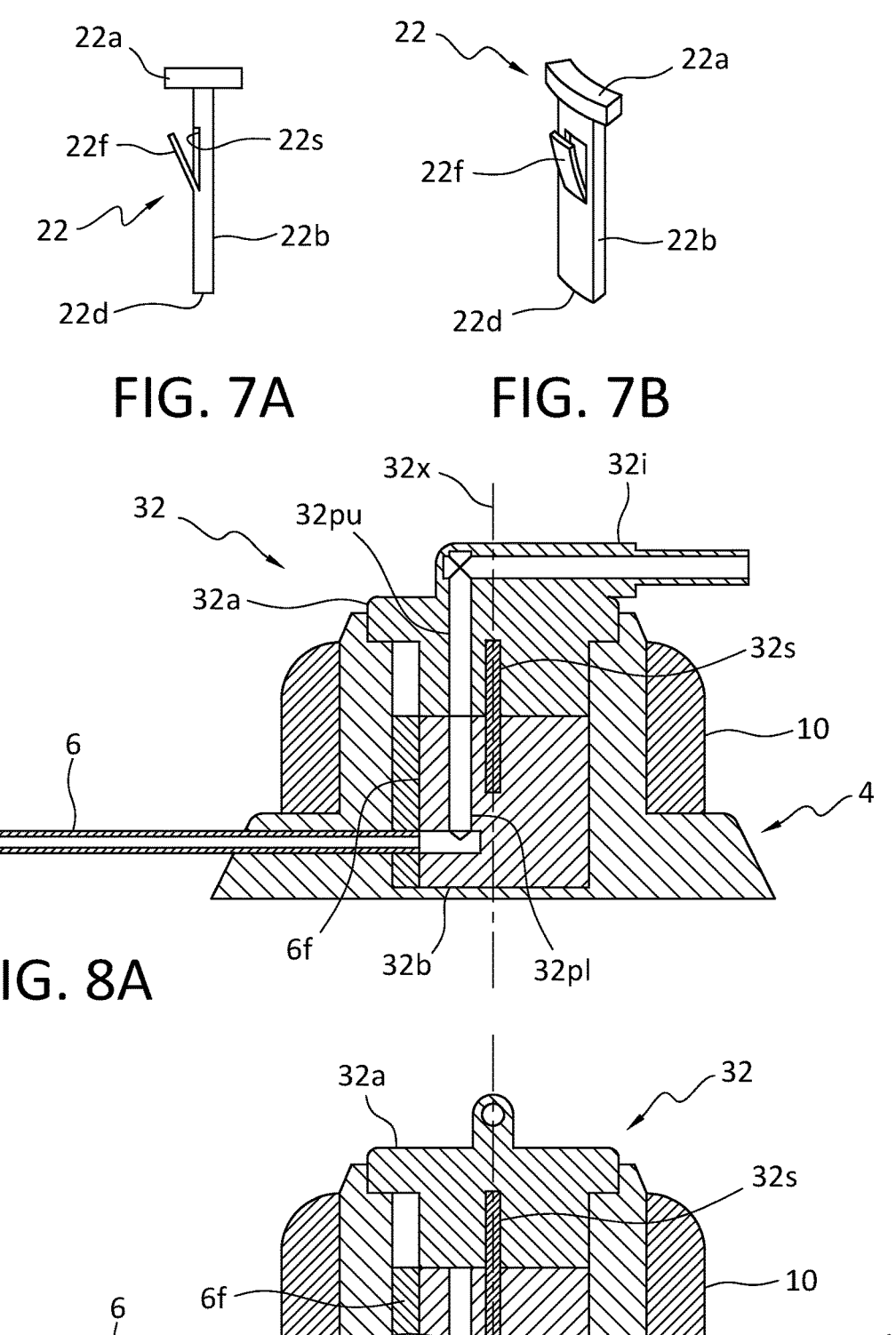
FIGS. 7A-7B show side and perspective views, respectively, of the exemplar tool.
FIGS. 8A-8B illustrate another embodiment of the inventive insert.

FIGS. 8A and 8B illustrate another embodiment of the inventive insert that may be used without having to be removed and replaced with a blank insert when the patient is not being infused. As shown, insert 32 has an upper portion 32*a* with an upper passageway 32*pu* and a lower portion 32*b* with a lower passageway 32*pl* that are rotatable relative to each other about a center shaft 32*s*. For discussion, it is assumed that passageways 32*pu* and 32*pl* are offset longitudinally from the center axis 32*x* of insert 32 and that shaft 32*s* lies along the longitudinal central axis 32*x*. For this embodiment, only lower portion 32*b* has a guide slot and flange 6*f* at housing 4 has a height that matches the height of the guide slot of lower portion 32*b*. Thus, once fully sealingly mated to the interior chamber of housing 4, upper portion 32*a* is rotatable relative to lower portion 32*b*, which includes the fluid outlet that remains in sealing alignment with the inlet of the lumen. To rotate upper portion 32*a*, a torque greater than a predetermined force that overcomes the frictional and sealing contact preventing the upper and lower portions from freely rotating relative to each other is applied against upper portion 32*a*. Insert 32 accordingly operates the same as insert 8 during infusion, as upper and lower passageways 32*pu* and 32*pl* are in alignment as per shown in FIG. 8A. At the end of the infusion procedure or during respite from infusion, upper portion 32*a* may be held by the integral part of the infusion inlet and rotate for example a counterclockwise 90° relative to lower portion 32*b* so that the fluid inlet is positioned in the direction into the paper as per shown in FIG. 8B. As a result, upper passageway 32*pu* and lower passageway 32*pl* are not in alignment with each other. This is illustrated in FIG. 8B where upper passageway 32*pu* is hidden from view. Upper portion 32*a* may be rotated back to its position as shown in FIG. 8A were infusion to resume.

Inasmuch as the present invention is subject to many variations, modifications and changes in detail, it is intended that all matter described in this specification and shown in the accompanying drawings be interpreted as illustrative only and not in a limited sense. For example, instead of the mechanical locking arrangement as described above, other locking arrangements including for example magnetic where a blank insert may be fitted with a magnet that enables it to be removed magnetically, or electronic by using a smart device that is available only to the clinician to deactivate the locking mechanism in the port. Also, the insert may be fitted into the housing by being screwed thereinto. In this case, counterpart screw threads are formed at the outer wall of the insert and the inner wall of the chamber of the housing. Accordingly, it is intended that the invention be limited only by the spirit and scope of the hereto appended claims.

The invention claimed is:
1. A port comprising:
a housing having an interior defined by a bottom, a non-ending wall and a top that has an opening that opens to the interior of the housing;
at least one aperture at a selected location through the non-ending wall;
an insert having a body structure with a top surface, a cross dimension and a depth that enables it to matingly fit to the interior of the housing via the opening of the housing, the top surface of the insert in substantial planar relationship with the top of the housing after insertion to the housing;
wherein the housing of the port is adapted to be implanted into a body with the top surface of the insert accessible from environment.

2. The port of claim 1, wherein the insert comprises a cylinder having a passageway extending from the top surface to an outlet at a sidewall of the insert in sealing alignment with the aperture to establish a fluid path between the top surface of the insert and the aperture when the insert is fitted to the housing.

3. The port of claim 2, further comprising a lumen having a proximal end removably attached to the aperture and a distal end that extends away from the housing and adapted to be selectively positioned to a location inside the body to output fluid to the location.

4. The port of claim 2, further comprising a tube extending from the aperture away from the housing, the tube adapted to removably accept a catheter slidably extending therethrough, the catheter having a distal end selectively positionable to a location inside the body, the catheter once used is removable from the tube and be replaced by another catheter.

5. The port of claim 2, wherein the passageway at the top surface of the insert has an inlet fluidly connected to the passageway for accepting an outlet of a fluid store, so that fluid from the fluid store may be infused through the passageway in the insert to a selected location in the body via a lumen having a proximal end attached to the aperture in alignment with the outlet of the insert and a distal end positioned at the selected location.

6. The port of claim 1, wherein the non-ending wall has an outer surface, the port further comprising tissue ingrowth media encircling at least the outer surface of the non-ending wall to enable tissue growth about the non-ending wall so that an aseptic barrier is formed where the non-ending wall and tissue of the body encircling the non-ending wall meet.

7. The port of claim 1, wherein the insert is a cylindrical blank plug that seals the interior of the housing when the port is not used for infusion and is a cylindrical infusion plug when the port is used for infusion, the cylindrical infusion plug having at least one inlet at its top surface and at least one passageway that extends from the one inlet to at least one outlet that comes into alignment with the one aperture to establish at least one fluid path from the one inlet to the one aperture, a lumen extending from the one aperture positionable to a selected location in the body to direct fluid input to the one inlet to the selected location.

8. The port of claim 1, wherein the insert fitted to the housing has a fixed lower portion and an upper portion rotatable relative to the lower portion, a through passageway extending from a fluid inlet at the top surface through the upper and lower portions to the one aperture, the passageway forming a fluid path from the fluid inlet to the one aperture when the upper and lower portions are in alignment with each other, the fluid path being interrupted when the upper portion and the lower portion are not in alignment with each other when the upper portion is rotated to a non-alignment position relative to the lower portion.

9. The port of claim 1, further comprising respective locking portions at the insert and housing that prevent the insert and housing from being tampered with or inadvertency separating from each other once the insert is fully fitted to the housing.

10. A port adapted to be implanted into a body while leaving a portion thereof viewable visually, comprising:
a housing having an interior defined by a bottom, a non-ending wall having an outer surface and a top that has an opening that opens to the interior of the housing;
at least one lumen extending from at least one aperture at the non-ending wall away from the housing;

an insert having a body structure with a top surface, a cross dimension and a depth that enables it to matingly fit to the interior of the housing via the opening of the housing;

wherein the housing of the port is adapted to be implantable into the body to a depth where the top surface of the insert is viewable visually.

11. The port of claim 10, further comprising tissue ingrowth media encircling at least the outer surface of the non-ending wall to form an aseptic barrier where the non-ending wall of the implanted housing and tissue of the body meet.

12. The port of claim 10, wherein the insert comprises a cylinder having a passageway extending from an inlet at the top surface to an outlet at a sidewall of the insert in alignment with the one aperture to establish at least one fluid path between the inlet and the one lumen extending from the one aperture when the insert is fitted to the housing.

13. The port of claim 10, wherein the insert has at least two passageways extending from two fluid inlets at the top surface to two outlets at the insert, the two outlets in alignment with two corresponding apertures at the housing to establish at least two fluid paths between the two fluid inlets and two corresponding lumens each extending from a corresponding one of the apertures when the insert is fitted to the housing.

14. The port of claim 10, wherein the at least one lumen comprises a proximal end removably anchored to the one aperture and a distal end that extends away from the housing so as to be selectively positioned to a location inside the body.

15. The port of claim 10, wherein the lumen comprises a catheter slidably fitted along a tube anchored to the one aperture, the catheter having a distal end selectively positionable to a location inside the body, the catheter once used is removable from the tube and be replaced by another catheter.

16. The port of claim 12, wherein the proximal end of the one lumen is removably anchored to the one aperture and includes a flange removably mated to a slot at an inner surface of the non-ending wall, the flange acting as a guide for the fitting of the insert to the interior of the housing and prevents rotational movement of the insert relative to the housing so that the outlet of the insert and the proximal end of the lumen remain in alignment after the insert is fitted to the interior of the housing.

17. The port of claim 10, wherein the insert is a cylindrical blank plug that seals the interior of the housing when the port is not used for infusion and is a cylindrical infusion plug when the port is used for infusion, the cylindrical infusion plug having an inlet at its top surface and a passageway that extends from the inlet to an outlet in sealing alignment with the one aperture to establish a fluid path from the inlet to the one lumen extending from the aperture.

18. A port viewable visually and accessible from environment after implantation, comprising:

a housing having an interior defined by a bottom, a non-ending wall having an outer surface and a top that has an opening that opens to the interior of the housing;

at least one lumen extending from at least one aperture at the non-ending wall;

tissue ingrowth media encircling the outer surface of the non-ending wall;

an insert having a body structure with a top surface, a cross dimension and a depth that enable the insert to be matingly fitted into the interior of the housing via the opening of the housing;

wherein the housing of the port is implantable into a body to a depth where the top surface of the insert remains accessible from the environment; and wherein once implanted to the body, the tissue ingrowth media forms an aseptic barrier between the non-ending wall and tissue of the body encircling the wall.

19. The port of claim 18, wherein the insert is a cylindrical blank plug that seals the interior of the housing when the port is not used for infusion and is an infusion plug when the port is used for infusion, the infusion plug having at least one inlet at its top surface and at least one passageway that extends from the one inlet to at least one outlet in sealing alignment with the one aperture to establish at least one fluid path from the one inlet to the one lumen extending from the one aperture.

20. The port of claim 18, wherein the insert comprises a cylinder having a first passageway extending from a first inlet at the top surface to the one lumen via a first outlet at the insert in alignment with the one aperture and a second passageway extending from a second inlet at the top surface to an other lumen extending from an other aperture at the non-ending wall via a second outlet at the insert in alignment with the other aperture so that two passageways are provided when the insert is fitted to the housing.

* * * * *